United States Patent [19]

Magin

[11] 4,243,591

[45] Jan. 6, 1981

[54] POLY(VINYL PHOSPHONOMETHYLENE AMINO CARBOXYLATES) AND PROCESS FOR PREPARATION

[75] Inventor: Ralph W. Magin, Chesterfield, Mo.

[73] Assignee: Monsanto Company, St. Louis, Mo.

[21] Appl. No.: 16,859

[22] Filed: Mar. 2, 1979

Related U.S. Application Data

[63] Continuation-in-part of Ser. No. 783,360, Mar. 31, 1977, abandoned, and a continuation-in-part of Ser. No. 723,390, Sep. 15, 1976, abandoned, and a continuation of Ser. No. 630,231, Nov. 10, 1975, abandoned.

[51] Int. Cl.$^3$ .................. C07D 401/14; C07D 403/14
[52] U.S. Cl. .................. 260/326.22; 260/239.3 R; 260/326.25; 260/326.1; 260/429 R; 260/429.7; 260/429.9; 260/439 R; 260/502.5; 546/6; 546/22
[58] Field of Search .......... 260/326.25, 502.5, 326.22, 260/326.1, 239.3 R, 429.7, 429.9, 429 R, 439 R; 546/6, 22

[56] References Cited

U.S. PATENT DOCUMENTS

| | | | |
|---|---|---|---|
| 2,579,810 | 12/1951 | Fields | 260/502.5 |
| 2,609,390 | 9/1952 | Bersworth | 260/502.5 |
| 2,841,611 | 7/1958 | Bersworth | 260/502.5 |
| 3,288,846 | 11/1966 | Irani et al. | 260/502.5 |
| 3,293,152 | 12/1966 | Herbert | 252/180 |
| 3,322,716 | 5/1967 | Klein | 260/502.5 |
| 3,331,773 | 7/1967 | Gunderson et al. | 252/180 |
| 3,434,969 | 3/1969 | Rolston | 260/502.5 |
| 3,505,238 | 4/1970 | Teddell | 252/180 |
| 3,647,782 | 3/1972 | Collins | 260/502.5 |
| 3,699,048 | 10/1972 | Krueger et al. | 252/180 |
| 3,799,893 | 3/1974 | Quinlan | 260/502.5 |
| 3,816,333 | 6/1974 | King et al. | 260/502.5 |
| 4,002,672 | 1/1977 | Smith | 260/502.5 |
| 4,025,332 | 5/1977 | Franz | 260/502.5 |
| 4,033,896 | 7/1977 | Mitchell et al. | 260/502.5 |
| 4,035,412 | 7/1977 | Quinlan | 260/502.5 |
| 4,047,927 | 9/1977 | Gaertner et al. | 260/502.5 |
| 4,062,669 | 12/1977 | Franz | 546/22 |
| 4,079,000 | 3/1978 | Mitchell | 260/502.5 |
| 4,119,430 | 10/1978 | Gaertner et al. | 260/502.5 |
| 4,147,719 | 4/1979 | Franz | 546/22 |

*Primary Examiner*—Mary C. Lee
*Attorney, Agent, or Firm*—George R. Beck

[57] ABSTRACT

Poly(vinyl phosphonomethylene amino carboxylates) having at least one N-C-P linkage and at least one carboxyl end group per molecule are prepared by reacting a polyvinyl cyclic amide, orthophosphorous acid and formaldehyde in an aqueous acidic mixture at a temperature in excess of about 70° C. The resulting polymeric compounds are useful as metal complexing agents and in water treating to inhibit scale formation and corrosion of metals by oxygen-containing waters.

18 Claims, No Drawings

POLY(VINYL PHOSPHONOMETHYLENE AMINO CARBOXYLATES) AND PROCESS FOR PREPARATION

RELATED APPLICATIONS

This is a continuation-in-part of application Ser. No. 783,360 filed Mar. 31, 1977, now abandoned, a continuation-in-part of application Ser. No. 723,390 filed Sept. 15, 1976, now abandoned, a continuation of application Ser. No. 630,231 filed Nov. 10, 1975, now abandoned.

BACKGROUND OF THE INVENTION

The Mannich reaction for the condensation of ammonia or a primary or secondary amine with formaldehyde and a compound containing at least one reactive hydrogen atom is well known and described, for example, in Blicke: ORGANIC REACTIONS, 1, 304–330, (1954). Application of the Mannich reaction to the preparation of aminoalkylene phosphonic acid compounds has been discussed in Fields: J. AM. CHEM. SOC., 74, 1528–1531 (1952), which discloses preparation of esters of N-substituted aminomethyl phosphonic acids by reacting an aldehyde or ketone with a mixture of a phosphite diester and a primary or secondary amine, and Frank: CHEM. REVIEWS, 61, 392–394 (August 1961) which discloses preparation of aminomethyl phosphonous acids by reaction of a mixture of hypophosphorous acid, a primary amine and a carbonyl compound which may be an aldehyde or ketone. These and other references are cited in U.S. Pat. No. 3,288,846 which teaches direct preparation of aminomethylene phosphonic acids by reaction of formaldehyde, ammonia or an amine and orthophosphorous acid. Monomeric phosphonomethylene aminomethylene carboxylate is known and has been suggested for use as a corrosion inhibitor (U.S. Pat. No. 3,483,133) and as a scale inhibitor for saline water systems (U.S. Pat. No. 3,505,238).

Although prior art products provide satisfactory results when used in water treating applications as scale inhibitors and/or corrosion inhibitors, there is now provided a new class of materials that have a unique structure. These materials are effective metal ion sequestrants and are useful in water treating applications as scale and/or corrosion inhibitors. The materials of the present invention not only are polymeric, but contain a carboxylate group as well as a phosphonate group. This combination within one molecule provides utility superior to prior art products in many applications.

SUMMARY

According to the present invention, there is provided a polyvinyl compound having the formula:

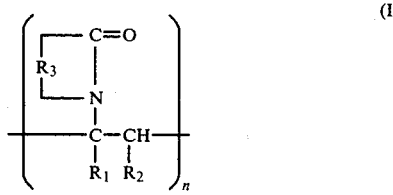

(I)

wherein $R_1$ and $R_2$ are individually selected from the group consisting of hydrogen, phenyl and alkyl having from 1 to about 4 carbon atoms; $R_3$ is selected from the group consisting of alkylene, alkylenylene, arylene, alkarylene, and bicycloalkylene radicals having from about 3 to about 15 carbon atoms; and n is an integer from about 4 to about 2,000; wherein each of from one to n of the cyclic amide groups in said polymer has been replaced with a phosphonomethylene amino carboxylate group having the formula:

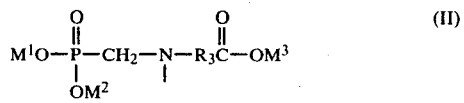

(II)

wherein $M^1$, $M^2$ and $M^3$ are individually selected from the group consisting of hydrogen, a metallic element, ammonium and alkyl ammonium having up to about 10 carbon atoms.

Broadly described, the above polyvinyl compound wherein at least one cyclic amide has been replaced by a phosphonomethylene amino carboxylate group (hereinafter referred to as "PVPAC") is prepared by heating an aqueous mixture of polyvinyl cyclic amide, formaldehyde and orthophosphorous acid (or $PCl_3$ and water) at a pH less than about 4 to a temperature greater than about 70° C. for a time sufficient to form a polymeric reaction product having at least one N-C-P linkage and a carboxyl end group.

Polyvinyl cyclic amides (sometimes referred to as "polymeric alkenyl cyclic amides") useful to make PVPAC of the present invention are known to the art, and have the general formula I above. Such amides may be prepared as suggested in ACETYLENE AND CARBON MONOXIDE CHEMISTRY, Copenhaver and Bigelow, Reinhold Publishing Corp., New York, pages 66–90 (1949).

Many variations in specific structure of the polyvinyl cyclic amides of Formula I are possible through variations in $R_1$, $R_2$ and $R_3$. In general, $R_3$ may be any divalent organic radical in the cyclic amide portion of the polymer. With respect to $R_1$ and $R_2$, useful radicals include hydrogen, phenyl and any alkyl group having from one to about four carbon atoms, which radicals constitute substituents on the "backbone" of the vinyl polymeric chain. The particular substituents depend on the substituted acetylene employed to produce the vinyl-substituted cyclic amide which is polymerized to produce the polyvinyl cyclic amide starting material. In addition to acetylene itself, suitable substituted acetylenes include methyl acetylene, ethyl acetylene, propyl acetylene, butyl acetylene, dimethyl acetylene, phenyl acetylene, phenyl methyl acetylene, diphenyl acetylene and the like. Thus $R_1$ and $R_2$ can be any of the above alkyl or phenyl substituents. Polyvinyl cyclic amides wherein both $R_1$ and $R_2$ are hydrogen are usually preferred.

With respect to $R_3$, which may be any organic radical in the cyclic amide portion of the polymer, useful alkylene and alkenylene radicals are those having from about 3 to about 15 carbon atoms and may be aliphatic or alicyclic, the alicyclic radicals usually containing from about 4 to about 10 carbon atoms. Useful arylene radicals are phenylene and naphthylene radicals. The $R_3$ radicals may be unsubstituted or substituted, e.g. with $C_{1-6}$ alkyl, hydroxyl or halogen (chlorine, fluorine or bromine).

As described above, n can be any integer from about 4 to about 2,000, i.e., before any phosphonomethylation the polyvinyl cyclic amide can have a molecular weight (MW) from about 444 to about 222,000. The resulting PVPAC will possess correspondingly higher MW (at least about 560) reflecting phosphonomethylation of the respective starting polyvinyl cyclic amides. Preferably n is from about 4 to about 1,000 and, for many of the uses disclosed herein, from about 4 to about 200. In most instances satisfactory results are obtained when n is at least about 10.

Suitable polyvinyl cyclic amides for use in the process of the present invention to make PVPAC include:

Polyvinyl pyrrolidone (III)

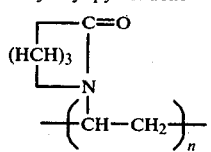

Polyvinyl piperidone (IV)

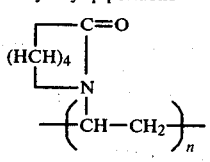

Polyvinyl caprolactam (V)

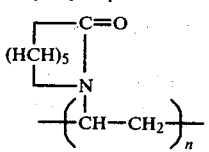

Polyvinyl dodecyl lactam (VI)

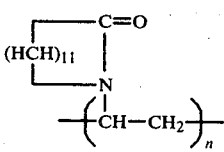

Polyvinyl bicyclo (2.2.2)-2-azaoctan-3-one (VII)

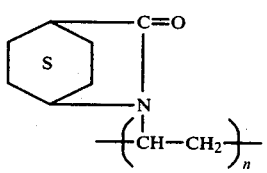

Polyvinyl benzpyrrolidone (VIII)

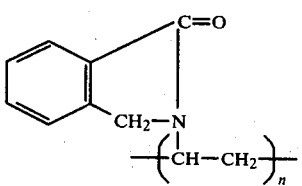

Polymethylvinyl pyrrolidone (Polyallylene pyrrolidone) (IX)

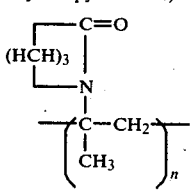

Polyphenylvinyl pyrrolidone (Polyacetenyl benzene pyrrolidone) (X)

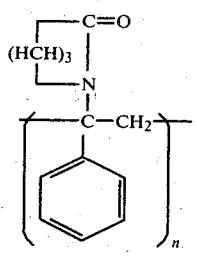

Particularly preferred polymeric alkenyl cyclic amides are polyvinyl lactams having the general formula

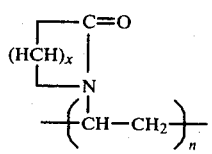

wherein x is from about 3 to about 5, with polyvinyl pyrrolidone (III) particularly preferred as a readily available, low-cost reactant.

Formaldehyde (or paraformaldehyde) useful in the present invention to prepare PVPAC can be used per se or mixed with alcohols and/or water to facilitate handling of the reaction mass, temperature control and prevention of foaming. For example, Formalin, a trademark for a 27% (United States) or 40% (British) formaldehyde solution, is an aqueous solution generally containing from about 0% to about 40% methanol.

The phosphorus-containing compound which serves as a reactant in the present invention to prepare PVPAC compounds is orthophosphorous acid. It is generally preferred, however, to employ $PCl_3$ and $H_2O$ which react to make orthophosphorous acid. These ingredients can be used separately and even added at different points of the manufacturing process, if desired.

Orthophosphorous acid can be utilized in the process of the present invention as either the acid or one of its salts, such as its mono- or di(alkali metal) salts. Such salts will generally be utilized in combination with an amount of a supplementary acid sufficient to maintain pH of the reaction mixture below about 4 and convert the orthophosphorous acid salt into a more reactive acid form. The supplementary acid may be any strong acid, e.g. hydrochloric, sulfuric, hydrobromic, phosphoric or a sulfonic acid. For ease of description, the remainder of the specification will generally refer to orthophosphorous acid as the phosphorus-containing reactant.

The PVPAC compounds of the present invention are prepared by reacting orthophosphorous acid, formaldehyde and the polyvinyl cyclic amide in an aqueous mixture at elevated temperature. The mixture preferably contains from about 5 to about 75% (most preferably from about 30 to about 50%) water to promote the reaction and facilitate mixing, handling, and heat transfer. The rate of reaction increases with increasing temperature and the reaction temperature is preferably maintained above about 85° C. and most preferably at about reaction reflux temperature. Temperatures up to about 200° C. may be employed but temperatures in excess of 200° C. should be avoided to prevent decomposition of the orthophosphorous acid.

The pH of the reaction affects the rate of the desired reaction and formation of by-products. The pH is preferably maintained below about 4 and most preferably below about 2 to maximize formation of PVPAC and minimize oxidation of phosphorous acid to phosphoric acid. The pH of the reaction medium is readily adjusted by addition of HCl or other strong acid, e.g. sulfuric, a sulfonic, hydrobromic or phosphoric acids.

The reaction preferably employs a catalytic amount of a halide ion to inhibit oxidation of the orthophosphorous acid and improve yields of the desired reaction product. Although any halide may be used, chloride is preferred. HCl is a convenient source and serves the dual function of reducing pH of the reaction mixture. The halide ion is preferably present in amounts of from about 0.01 to 10% by weight, and more preferably from 0.5 to about 3% by weight. Most preferably there is an amount of halide ion at least equimolar to the amide groups present.

Catalysts which may be used in place of the preferred chloride ion include other halides (fluoride, bromide and iodide) as well as sulfate and sulfite ions. These ions may be supplied in the form of acids or salts.

The reaction time and sequence of addition of reactants is important in the process for preparing PVPAC. Although PVPAC will be obtained if the reactants are simply combined and maintained at desired pH and temperature from about 1 to about 7 hours or longer, such a method results in considerable by-product formation which is believed to include the oxidation of orthophosphorous acid to orthophosphoric acid and/or formation of hydroxymethylene phosphonic acid. While PVPAC may be refined to remove these secondary products, in most instances purification is not necessary as their presence in the PVPAC is not detrimental. The loss of orthophosphorous acid and formaldehyde due to these side reactions may be compensated by adding a slight excess of these materials for the desired reaction.

It is important that the polyvinyl compounds of this invention contain at least one phosphonomethylene amino carboxylate group, because this group is responsible for the properties of the PVPAC of the present invention. It is preferred that the polyvinyl compound contain at least 5% phosphonomethylene amino carboxylate groups, based on the number of amide groups in the polyvinyl cyclic amide starting material, and even more preferred that the proportion of phosphonomethylene amino carboxylate groups is at least about 10% on that same basis. All of the amide groups can be converted to phosphonomethylene amino carboxylate groups in accordance with the present invention, although complete conversion may be difficult from an economical standpoint.

The reaction as described is the preparation of the acid form of the PVPAC compounds. Salt forms are easily prepared by reacting the resulting acids with a base which may be a metal hydroxide or ammonium compound, so that $M_1$, $M_2$ and $M_3$ of Formula II can be individually selected from hydrogen, a metallic element, ammonium and alkyl ammonium containing up to about 10 carbon atoms. With respect to $M_1$, $M_2$ and $M_3$, useful metallic elements include, e.g. alkali metals such as sodium, lithium and potassium; alkaline earth metals such as calcium and magnesium; and other metallic elements such as aluminum, zinc, cadmium, manganese, nickel, cobalt, lead, tin, iron, chromium and copper. The preferred ions are those which produce a salt soluble in water in concentrations sufficient for the desired applications, the generally preferred ions being sodium, potassium, ammonium and zinc. $M_1$, $M_2$ and $M_3$ represent monovalent metal ions on a one-to-one basis. In the case of divalent or trivalent metal ions, each ion constitutes two or three M radicals, respectively, which may be any combination of $M_1$, $M_2$ and $M_3$ and may be from the same or different units of the polymer.

In addition to ammonium, useful alkyl ammonium radicals are those derived from amines having a MW being about 300 and more particularly from alkyl amines, alkylene polyamines and alkanol amines containing from 1 to about 10 carbon atoms such as, for example, ethyl amine, diethyl amine, ethylene diamine, diethylene triamine, triethylamine, propyl amine, propylene diamine, hexyl amine, 2-ethylhexylamine, N-butylethanol amine, triethanol amine, hexamethylenediamine, etc.

The acid and salt forms of the PVPAC of the present invention have utility in treating water or aqueous systems and function as sequestering agents, "threshold" agents and/or corrosion inhibitors. Sequestration is accomplished by adding at least a stoichiometric amount of the PVPAC as required to complex the metal ions present in the system. The term "threshold" as utilized herein refers to the phenomenon that less than stoichiometric quantities of the PVPAC can present precipitation and/or alter the crystal forms of various salts of metals such as calcium, iron, copper, cobalt, etc. Normally in such "threshold" treatment of water, from about 0.05 to about 500 ppm and preferably from about 0.5 to about 25 ppm, are added to the aqueous system to interfere with the growth of crystal nuclei and thereby prevent deposition of insoluble deposits.

This is discussed in publications such as U.S. Pat. No. 2,038,316 and articles by Reitmeier and Buehrer in 44 J. Phys. Chem. 535–74 (1939). Additional explanation is found in publications of Hatch and Rice appearing in Ind. Eng. and Chem., January 1939 and August 1945.

PVPAC of the present invention has utility to inhibit precipitation of metal ions from aqueous solutions and/or alter those crystals formed such that the adherence to surfaces is substantially reduced. Typical applications include liquid soaps and shampoos (U.S. Pat. No. 3,313,735); bar soaps; scouring wool cloth; cotton kier boiling; cotton dyeing; cotton bleaching; metal cleaning compounds; rubber and plastics metal contamination (compounding and polymerization); pulp and paper metal contamination; saline water (U.S. Pat. No. 3,505,238); photographic developers (U.S. Pat. No. 3,201,246); hair bleaching and dyeing operations (U.S. Pat. No. 3,202,579); stabilizing hydrogen peroxide solutions (U.S. Pat. No. 3,385,675); brackish water; squeeze treatment of oil wells (U.S. Pat. No. 3,483,925); and control of mineral (e.g. $BaSO_4$) scale in oil wells.

The amount of PVPAC needed to be effective varies with the type and amount of problem metal ions, pH conditions, temperature and the like. When using substoichiometric ("threshold") amounts, the preferred mole ratio of precipitation inhibitor to scale forming cations is from about 1:1.5 to about 1:10,000. When using sequestering amounts, i.e., at least stoichiometric quantities, the preferred mole ratio is from about 1:1 to 2.5:1 relative to the metal ions in the aqueous system.

It is within the present invention that PVPAC may be used in aqueous systems which contain various inorganic and/or organic materials (particularly ingredients or substances used by the water-treating industry) with the proviso that such materials do not render the PVPAC ineffective for its purpose disclosed herein. These materials include, without limitation, polycarboxylates, particularly those of molecular weight from about 1,000 to about 100,000; antifoam agents; water-soluble polymers such as polyacrylic acid, polyacrylamide, partially hydrolyzed acrylamide and the like; tannins; lignins; deaerating materials; polymeric anhydrides, e.g. salts of hydrolyzed polymaleic anhydride; sulfonated lignins and salts thereof. Other materials useful with said inhibitors include, e.g. surface active agents, acetodiphosphonic acids, inorganic phosphates including orthophosphates, molecularly dehydrated phosphates and phosphonates, polyfunctional phosphated polyol esters, inorganic silicates and calcium and magnesium salts such as chlorides, sulfates, nitrates and bicarbonates. Furthermore, other scale and precipitation inhibitors, e.g. polyphosphonates such as amino tri(methylene phosphonic acid), may be used with PVPAC of the present invention. For exemplary purposes only, such other precipitation inhibitors are described in U.S. Pat. Nos. 3,234,124; 3,336,221; 3,393,150; 3,400,078; 3,400,148; 3,434,969; 3,451,939; 3,462,365; 3,480,083; 3,591,513; 3,597,352 and 3,644,205. Other corrosion inhibitors can also be used in combination with the PVPAC of the present invention, including those described in U.S. Pat. Nos. 3,483,133; 3,487,018; 3,518,203; 3,532,639; 3,580,855; and 3,592,764.

PVPAC of the present invention inhibits corrosion of metal surfaces in contact with aqueous corrosive media, and particularly oxygen-bearing waters. It has been found that to effectively inhibit corrosion at least about 3 ppm, preferably from about 10 ppm to about 500 ppm, and more preferably from about 10 to about 150 ppm of the PVPAC compound should be included in the corrosive medium. It is to be understood that greater than 500 ppm can be used if desired. Amounts as low as about 1 ppm are effective under some conditions.

The PVPAC corrosion inhibitors of the present invention are effective in acidic and basic corrosive media. The pH can range from about 4 to about 12. In cooling towers the water system is generally maintained at a pH from about 6.5 to about 10, and most often at a pH from about 6.5 to about 8.5. In all such systems, the inhibitors of the present invention are normally effective.

In addition to utilization of the PVPAC's of the present invention as corrosion inhibitors, they may be successfully employed together with zinc ion or chromates or dichromates. That is, use of the PVPAC with zinc ion, chromate or dichromate, or both zinc ion and a chromate or dichromate effectively inhibits corrosion. The zinc ion and chromate or dichromate are preferably used in roughly the same concentrations as the PVPAC, e.g. from about 1 to about 100 ppm zinc ion and/or about 1 to about 100 ppm chromate or dichromate, and preferably from about 5 to about 25 ppm zinc ion and/or about 5 to about 25 ppm chromate or dichromate. The present invention also encompasses a corrosion inhibiting process utilizing mixtures of the PVPAC of this invention and a zinc-containing material capable of forming the zinc ion in aqueous media and/or a water-soluble compound of hexavalent chromium, preferably an alkali metal or ammonium chromate or dichromate or chromic acid.

Where the water systems are in contact with various metals such as iron or copper, it is frequently desirable to use, along with the PVPAC, either alone or in combination with zinc and/or chromium ions, a 1,2,3-triazole or a thiol or a thiazole, an oxazole or imidazole such as are known to inhibit corrosion of copper. These azoles are likewise effective with PVPAC of the present invention. The amounts of azoles desirably used depend on the particular aqueous systems. Generally, concentrations of about 0.05 to about 5 ppm thiol or triazole with from about 3 to about 100 ppm PVPAC and up to about 100 ppm zinc ion are satisfactory, and concentrations from about 0.5 to about 2 ppm of the azole with from about 5 to about 25 ppm PVPAC and, if desired, from about 5 to about 25 ppm zinc ion, are preferred.

DESCRIPTION OF PREFERRED EMBODIMENTS

In a preferred embodiment of the present invention, orthophosphorous acid and polyvinyl cyclic amide are combined in a ratio of at least one mole of such acid for each mole of cyclic amide group, and an excess of orthophosphorous acid may be used. The reactants are heated to at least about 85° C., preferably to the refluxing temperature of the mixture, and maintained at this temperature for an induction period sufficiently long to hydrolyze the cyclic amide, produce an open ring and form the N-H group. Such period generally ranges from about 10 minutes to about 5 hours or longer, depending on the size of the ring and MW of the polymer. Following this period, formaldehyde is metered into the reaction media over a period from about 10 minutes to about 3 hours while stirring and maintaining pH and temperature at desired reaction conditions. Addition of at least one mole of formaldehyde per mole of cyclic amide should be made and a molar excess of formaldehyde may be used.

Following completion of the formaldehyde addition, the reactants are typically maintained at reaction temperature, preferably at reflux, for a time from about 10 minutes to about 2 hours or longer to allow the reaction to proceed to maximum completion.

The present invention is illustrated by, but not limited to, the following examples. All parts and percentages are by weight unless otherwise specified.

EXAMPLE I

Into a 500 ml flask equipped with an efficient stirrer, a water condenser and dropping funnel are charged 82 grams (0.5 mole) of 49.9% orthophosphorous acid containing 7.8 grams of HCl, and 57 grams of 37% hydrochloric acid. The total moles of HCl is 1.0. To the mixture is added 70 grams of polyvinyl pyrrolidone of approximately 10,000 MW in technical grade form. The reaction mass is then heated to boiling over a period of 10 minutes to obtain a homogeneous, clear solution having a boiling point of 110°-112° C.

The resultant clear solution in the flask is maintained at boiling for about two hours, and then over a period of one hour, 18 grams (0.55 mole) of paraformaldehyde is added. At the end of the one hour period the reaction mixture, which is a clear solution, is held at boiling with reflux for an additional 24 hours, sampled and then cooled to 25° C. The 230 grams of solution is clear with an amber color. The product is found to contain 38.24 grams of PVPAC equal to a yield of 16.6% of theory based on the cyclic amide reacted.

The specific $P^{31}$ NMR ppm chemical shift of the above product relative to phosphoric acid is found to be:

| ppm  | pH   | Linkage |
|------|------|---------|
| −7.5 | Acid | N-C-P   |

EXAMPLE II

The procedure of Example I is repeated substituting 70 grams of polyvinyl pyrrolidone of 160,000 MW. A total solution product containing 11.1 grams of phosphonated product is obtained for a yield of about 4.8% of theory based upon the starting polyvinyl pyrrolidone.

The $P^{31}$ NMR spectra, −7.5 ppm chemical shift, indicate the structure of the product to be the same as that obtained in Example I except for MW.

EXAMPLE III

The procedure of Example I is repeated substituting 80 grams of polymethyl vinyl pyrrolidone of approximately 14,500 MW for the polyvinyl pyrrolidone of Example I. A total solution product of 240 grams containing the PVPAC compound is obtained as determined by $P^{31}$ spectra.

EXAMPLE IV

The procedure of Example I is repeated substituting 120 grams of polyphenyl vinyl pyrrolidone of approximately 1800 MW for the polyvinyl pyrrolidone of Example I. A total solution product containing the PVPAC compound as determined by $P^{31}$ NMR spectra is obtained.

EXAMPLE V

The procedure of Example I is repeated substituting 94 grams of polyvinyl caprolactam of approximately 12,600 MW for the polyvinyl pyrrolidone of Example I. A total solution product containing PVPAC as determined by $P^{31}$ NMR spectra is obtained.

EXAMPLE VI

Into a 250 ml flask equipped with an efficient stirrer, a water condenser and dropping funnel are charged 14.5 grams of 37% hydrochloric acid and 41 grams of 49.9% orthophosphorous acid containing 3.90 grams of HCl. The total moles of HCl is 0.25. To the mixture is added 36 grams (0.25 mole) of polyvinyl bicyclo(2.2.2)-2-azaoctan-3-one. The reaction mass is then heated for about 20 minutes to boiling, obtaining a homogeneous, clear solution having a boiling point of 110° C.–115° C.

The resultant clear solution in the flask is maintained at boiling for 4 hours, and then over a period of 60 minutes, 8.7 grams (0.26 mole) of paraformaldehyde is added. At the end of the 60 minute period the reaction mixture, which is a clear to yellowamber solution, is held at boiling with reflux for an additional 2 hours and then is cooled to 25°–30° C. At 25°–30° C. the product is a slightly viscous yellow solution which does not crystallize. The $P^{31}$ NMR spectra of a sample indicates the reaction product contains PVPAC.

EXAMPLE VII

Into a 250 ml flask equipped with a water condenser and a dropping funnel are charged 33 grams (0.20 mole) of 49.9% orthophosphorous acid containing 3.1 grams of HCl, and 4.2 grams of 37% hydrochloric acid for a total of 7.3 grams (0.20 mole) of HCl. To the acid mixture is added 31.8 grams (0.20 mole) of polyvinyl benzpyrrolidone and 25 milliliters of water. The mixture is heated with stirring until solution is obtained and heating is continued until reflux is obtained at approximately 108° C.

The solution is maintained at reflux for one hour and then over a period of 2 hours there is slowly added 7.35 grams (0.22 mole) of 90% paraformaldehyde. After addition of formaldehyde the reaction mixture, which is a clear pale yellow solution, is held at reflux for an additional period of 6 hours. A sample taken for NMR analysis shows a typical ppm chemical shift at −9.3 and indicates that 10% of the cyclic amide has been converted to PVPAC of the present invention.

EXAMPLE VIII

The sequestering utility of the acids and salts of PVPAC prepared in accordance with Examples I–VII are determined by procedure described in COORDINATION CHEMISTRY, "Calcium Complexing by Phosphorus Compounds" by C. F. Callis et al., Plenum Press, pp. 223–40 (1969).

Approximately 1 gram of the PVPAC to be evaluated is mixed with 0.1% sodium oxalate in a 2-liter flask containing 100 ml water. The pH is adjusted to 11 by addition of NaOH. Into the test solution there is titrated 0.1 molar calcium nitrate solution via use of a Sargent-Malmstadt automatic titrator, Model SE, which also measures turbidity by light transmission. The amount of calcium nitrate added is sufficient to determine the point of inflection at which the sequestrant-containing solution changes from relatively clear to turbid. This inflection point is a measure of the amount of calcium sequestered by the PVPAC.

The sequestration test demonstrates that the PVPAC compounds of Examples I through VII are effective sequestering agents of calcium. Equivalent results are obtained with other PVPAC acids and salts.

EXAMPLE IX

PVPAC of the present invention falling within Formula I also exhibit threshold properties, i.e., in less than stoichiometric quantities they prevent precipitation of salts (e.g. $CaCO_3$) in aqueous systems. Specifically, a test is conducted in which the compounds of Examples I through VII are separately and independently mixed at 25° C. with 250 ml of water containing $NaHCO_3$. To the resultant mixture is added a concentrated $CaCl_2$ solution. The pH in each case is adjusted to and maintained at 8.5 with NaOH or HCl. The amounts of $CaCl_2$, $NaHCO_3$ and inhibiting agent are sufficient to provide 1600 ppm of $CaCO_3$ and 10 ppm of the indicated PVPAC precipitation inhibitor. It is observed in each case that these substoichiometric quantities effect a substantially clear solution for a period of at least 24 hours. Stating the results differently, 10 ppm of the indicated PVPAC is effective in providing a clear solution (essentially no precipitation) which contains substantially greater than stoichiometric quantities of $CaCO_3$. Analysis of aliquots of the solutions by titration with a standard solution of ethylene diamine tetraacetic acid using an Eriochrome Black T indicator establishes that at least 94% of all the $CaCO_3$ present remains in solution.

EXAMPLE X

An additional test of threshold inhibition of $CaSO_4$ by PVPAC is conducted in generally the same manner as in Example IX except that the test solutions contain 10,000 ppm CaSO$_4$ as well as 10 ppm of the specific inhibitors at a pH of 7. It is again observed that these PVPAC inhibitors or threshold agents maintain a substantially clear solution for a period of at least 24 hours. Analysis of samples of the solutions by the titration described above establishes that at least 97% of the CaSO$_4$ present remains in solution.

EXAMPLE XI

The ability of PVPAC compounds to act as threshold agents to inhibit precipitation of CaSO$_4$ at extremely low concentrations is demonstrated by preparing solutions of 10, 4, 2, 1, and 0.5 ppm inhibitor and 10,000 ppm CaSO$_4$ in deionized water, and adjusting the pH to 7 by addition of NaOH. The prepared samples are placed on a shaker and agitated throughout the test. Aliquots from duplicate samples are taken at designated intervals, and the calcium content remaining in solution determined by EDTA Eriochrome Black T titration of filtrate. From the amount of calcium remaining in an uninhibited solution, the % scale inhibition is determined.

When the PVPAC compound of Example I is evaluated in direct comparison with prior art nonpolymerics methylamino di(methylene phosphonic acid) and bis(-phosphonomethylene) aminopentamethylene carboxylate, both of which have been suggested for water treatment, the compound of Example I is surprisingly more effective as a threshold agent. The relative effectiveness of these compounds is shown by the following data taken after a 24 hour test:

| Additive, ppm | % CaSO$_4$ Scale Inhibition | | | | |
|---|---|---|---|---|---|
| | 10 | 4 | 2 | 1 | 0.5 |
| CH$_3$N(CH$_3$PO$_3$H$_2$)$_2$ | 100 | 98 | 70 | 5 | 4.5 |
| N(CH$_2$PO$_3$H$_2$)$_2$(CH$_2$)$_5$COOH | 93 | 96 | 87 | 11 | 5.5 |
| Example I Compound | 100 | 97 | 97 | 88 | 34 |

It is seen that even at only 1 ppm concentration, the compound of Example I maintains virtually all of the CaSO$_4$ in solution, compared to only 5% and 11% by the other compounds.

Comparable results in threshold inhibition of CaSO$_4$ precipitation are obtained with the other PVPAC acids and salts described herein. Accordingly, those compounds are useful to prevent scale formation in aqueous systems such as cooling tower waters.

EXAMPLE XII

The effectiveness of the PVPAC compounds of this invention as inhibitors of corrosion of metals by oxygenated waters is shown by tests determining metallic corrosion rates in polarization test cells employing steel electrodes with synthetic, very hard municipal water at an initial pH of 7 and continuous aeration. The concentrations of the inhibitors are calculated on the basis of active acid form of the PVPAC and the tests are carried out at inhibitor concentrations of 50 and 150 ppm in the hard water test medium. The rates of corrosion are determined by the Tafel Slope Extrapolation Method described in Chapter 8 of "Handbook of Corrosion, Testing and Evaluation" by Dean et al., Wiley-Intersciences, New York (1971) from the observed current densities and are expressed in terms of mils per year (mpy) of metal loss. The corrosion rates of the steel electrodes, when protected by the test concentrations of the corrosion inhibitors tested, can then be compared to the corrosion rates of those electrodes when unprotected by a corrosion inhibitor. The decrease in corrosion rate expressed in mpy indicates the effectiveness of the inhibitor. In tests of this nature, where the aqueous corrosion medium is synthetic hard municipal water at only slightly elevated temperature, any corrosion rate less than the corrosion rate of the medium alone is advantageous and rates of less than about 10 mpy are highly desired. Substances that give this rate or a lower rate are considered excellent.

The synthetic hard municipal water used in the test described is prepared to approximate hard municipal water as concentrated by operation of a cooling tower and composed of:

| Constituents | mg/l |
|---|---|
| Calcium | 88 |
| Magnesium | 24 |
| Chloride | 70 |
| Sulfate | 328 |
| Bicarbonate | 40 |
| Total hardness as CaCO$_3$ in distilled water | 319 |

The corrosion rates of a steel electrode at 35° C. in the synthetic hard municipal water medium described above adjusted to an initial pH of 7 without added inhibitor and containing the indicated concentrations of the compounds of Examples I and II are determined as discussed above by the Tafel Slope Extrapolation Method. Results are in Table II:

TABLE II

| Test Compound | Concentration of Corrosion Inhibitor (ppm) | Corrosion Rate (mpyy) |
|---|---|---|
| Control | None | 42 |
| I | 50 | 2 |
| | 150 | 2 |
| II | 50 | 3 |
| | 150 | 2 |

EXAMPLE XIII

Corrosion rate tests are conducted as in Example XII with compounds from Examples III through VII at the same two concentrations of active PVPAC. The results obtained show rates of corrosion ranging from about 2 to about 10 mpy in the same corrosive aerated synthetic water medium.

EXAMPLES XIV-XVII

In each of the following examples, the indicated PVPAC and zinc or chromate compounds are added to the corrosive aerated synthetic water medium of Example XII in amounts to supply 50 ppm of each indicated inhibitor.

| Example | Inhibitors |
|---|---|
| XIV | PVPAC of Example I and Zinc Sulfate |
| XV | PVPAC of Example III and Zinc Sulfate |
| XVI | PVPAC of Example V, Zinc Sulfate and Sodium Dichromate |
| XVII | PVPAC of Example VII, Zinc Sulfate and Sodium Dichromate |

The corrosion rates determined as in Examples XIV-XVII in all instances are lower than the untreated corrosive media and less than those obtained using only the PVPAC corrosion inhibitor.

EXAMPLE XVIII

A compressed ball of standard weight and dimension is prepared containing 38 parts of the PVPAC of Example I, 50 parts of leachable inert solids and 12 parts of a lignosulfite binder. After briquetting, this composition is suitable for mechanically measured addition in water treatment employing a ball feeder.

The corrosion inhibiting compounds of this invention can be employed in various forms which give good protection against corrosion. For example, the PVPAC compounds either in the form of acids or salts, alone or in combination with other corrosion inhibiting materials, e.g. as outlined above, including thiols, 1,2,3-triazoles, water-soluble zinc salts, chromates, silicates, inorganic phosphates, phosphonates, molybdates, tannins, lignins, lignin sulfonates and calcium and/or magnesium salts, can be simply dissolved by mixing them into the aqueous medium. In another method, they can be dissolved separately in water or other suitable solvent to form a solution which is then mixed with the aqueous medium.

Various means are available to insure that the correct proportion of corrosion inhibitor is present in the aqueous medium. For example, a solution containing the PVPAC can be metered into the aqueous medium by drop feeder. Another method is to formulate tablets or briquettes of a PVPAC with other solid ingredients, and these can be added to the aqueous medium. After briquetting, the formulation can be used in a standard ball feeder so that the formulation is released slowly into the aqueous medium.

I claim:
1. A polyvinyl compound having the formula:

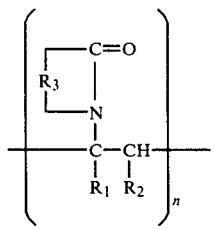

wherein $R_1$ and $R_2$ are individually selected from hydrogen, phenyl and alkyl having from 1 to about 4 carbon atoms; $R_3$ is selected from benzylene, phenylene, naphthylene and alkylene, radicals having from about 3 to about 15 carbon atoms, said radicals being unsubstituted or substituted with $C_1$-$C_6$ alkyl, hydroxyl, chlorine, fluorine or bromine; and n is an integer from about 4 to about 2,000; wherein each of from one to n of the cyclic amide group in said compound has been replaced with a phosphonomethylene amino carboxylate having the formula:

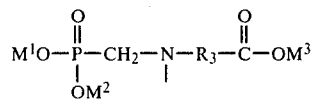

wherein $M^1$, $M^2$, and $M^3$ are individually selected from hydrogen, a metallic element, ammonium and alkyl ammonium having up to about 10 carbon atoms.

2. Compound of claim 1 wherein $R_3$ is unsubstituted.
3. Compound of claim 1 wherein at least 5% of the cyclic amide groups have been replaced with said phosphonomethylene amino carboxylate.
4. Compound of claim 2 wherein n is from about 4 to about 200.
5. Compound of claim 2 wherein $R_3$ is alkylene.
6. Compound of claim 5 wherein n is from about 10 to about 1000.
7. Compound of claim 6 wherein at least 5% of the cyclic amide groups have been replaced with said phosphonomethylene amino carboxylate.
8. Compound of claim 5 wherein $R_3$ is $+CH_2+_x$ in which x is from about 3 to about 5.
9. Compound of claim 8 wherein n is from about 4 to about 200.
10. Compound of claim 9 wherein $M^1$, $M^2$ and $M^3$ are individually selected from hydrogen, sodium, ammonium and potassium.
11. Compound of claim 9 wherein $M^1$, $M^2$ and $M^3$ are individually selected from one-half of a divalent metal on ion selected from zinc, calcium, magnesium, manganes, cadmium, tin and nickel.
12. Compound of claim 5 wherein $R_3$ is $+CH_2+_3$.
13. Compound of claim 12 wherein n is from about 4 to about 1,000.
14. Compound of claim 13 wherein at least 10% of the cyclic amide groups have been replaced with said phosphonomethylene amino carboxylate.
15. Compound of claim 14 wherein $R_1$ and $R_2$ are hydrogen.
16. Compound of claim 15 wherein n is from about 4 to about 200.
17. Compound of claim 15 wherein $M^1$, $M^2$ and $M^3$ are individually selected from hydrogen, sodium, ammonium and potassium.
18. Compound of claim 15 wherein $M^1$, $M^2$ and $M^3$ are individually selected from one-half of a divalent metal ion selected from zinc, calcium, magnesium, manganese, cadmium, tin and nickel.

* * * * *